(12) United States Patent
Biglari et al.

(10) Patent No.: US 11,249,037 B2
(45) Date of Patent: Feb. 15, 2022

(54) DEVICE AND METHOD FOR DETERMINING THE MICROSTRUCTURE OF A METAL PRODUCT, AND METALLURGICAL INSTALLATION

(71) Applicant: SMS GROUP GMBH, Düsseldorf (DE)

(72) Inventors: Mostafa Biglari, Mettmann (DE); Ulrich Sommers, Düsseldorf (DE); Christian Klinkenberg, Herdecke (DE); Michel Renard, Liege (BE); Guy Raymond, Ivoz-Ramet (BE); Oliver Pensis, Montegnee (BE); Tobias Terlau, Wülfrath (DE); Horst Krauthäuser, Heiligenhau (DE)

(73) Assignee: SMS GROUP GMBH, Düsseldorf (DE)

( * ) Notice: Subject to any disclaimer, the term of this patent is extended or adjusted under 35 U.S.C. 154(b) by 0 days.

(21) Appl. No.: 16/304,626

(22) PCT Filed: May 24, 2017

(86) PCT No.: PCT/EP2017/062527
§ 371 (c)(1),
(2) Date: Nov. 26, 2018

(87) PCT Pub. No.: WO2017/202904
PCT Pub. Date: Nov. 30, 2017

(65) Prior Publication Data
US 2019/0292624 A1    Sep. 26, 2019

(30) Foreign Application Priority Data

May 25, 2016  (DE) .................. 10 2016 209 181.6
May 19, 2017  (DE) .................. 10 2017 208 576.2

(51) Int. Cl.
*G01N 23/20008*   (2018.01)
*C21D 9/56*        (2006.01)
(Continued)

(52) U.S. Cl.
CPC ....... *G01N 23/20008* (2013.01); *C21D 9/562* (2013.01); *C21D 11/00* (2013.01);
(Continued)

(58) Field of Classification Search
CPC ....... G01N 23/20008; G01N 23/20033; G01N 2223/3103; G01N 2223/3307;
(Continued)

(56) References Cited

U.S. PATENT DOCUMENTS 4,982,417 A    1/1991   Kopineck et al.
7,617,709 B2  11/2009   Sano et al.
(Continued)

FOREIGN PATENT DOCUMENTS

DE    556383 C      8/1932
DE    2817742 B1   10/1979
(Continued)

OTHER PUBLICATIONS

Hermann-J. Kopineck et al: 11 Industrial on-line texture determination in rolled steel strips, Journal of Nondestructive Evaluation., vol. 12, No. 1, Mar. 1, 1993 (Mar. 1, 1993), pp. 13-19.
(Continued)

*Primary Examiner* — Scott R Kastler
(74) *Attorney, Agent, or Firm* — Lucas & Mercanti, LLP; Klaus P. Stoffel

(57) ABSTRACT

A device for determining the microstructure of a metal product during metallurgical production of the metal product, the device having at least one X-ray source, at least one X-ray detector and at least one accommodating chamber, inside which the X-ray source and/or the X-ray detector
(Continued)

is/are arranged and which has at least one window which is transparent to X-ray radiation. To allow reliable determination of the microstructure of a metal product during the metallurgical production thereof, the device includes at least one cooling installation for actively cooling the accommodating chamber.

12 Claims, 2 Drawing Sheets

(51) Int. Cl.
*C21D 11/00* (2006.01)
*G01N 23/20* (2018.01)
*G01N 33/204* (2019.01)
*B21B 1/00* (2006.01)
*B21B 38/02* (2006.01)

(52) U.S. Cl.
CPC .......... *G01N 23/20* (2013.01); *G01N 33/204* (2019.01); *B21B 1/00* (2013.01); *B21B 38/02* (2013.01); *C21D 9/56* (2013.01); *G01N 2223/308* (2013.01); *G01N 2223/3103* (2013.01); *G01N 2223/3307* (2013.01); *G01N 2223/3308* (2013.01); *G01N 2223/605* (2013.01); *G01N 2223/606* (2013.01); *G01N 2223/624* (2013.01); *G01N 2223/642* (2013.01); *G01N 2223/6462* (2013.01)

(58) Field of Classification Search
CPC ....... G01N 2223/605; G01N 2223/642; G01N 2223/6462; C21D 9/562; C21D 11/00
See application file for complete search history.

(56) References Cited

U.S. PATENT DOCUMENTS

| | | | |
|---|---|---|---|
| 10,077,942 B2 | 9/2018 | Hartung | |
| 2006/0117549 A1 | 6/2006 | Plocoennik | |
| 2015/0071409 A1* | 3/2015 | Gautsch | G01N 23/20016 378/80 |
| 2015/0158125 A1 | 6/2015 | Borgmann | |

FOREIGN PATENT DOCUMENTS

| | | |
|---|---|---|
| DE | 3825830 C2 | 2/1990 |
| DE | 112004002759 T5 | 2/2007 |
| EP | 0352423 B1 | 9/1993 |
| EP | 2674240 A1 | 12/2013 |
| GB | 2019559 B | 1/1983 |
| JP | 56001341 A | 1/1981 |
| JP | 61010749 A | 1/1986 |
| JP | 03817812 B2 | 9/2006 |
| WO | 2004050923 A1 | 6/2004 |
| WO | 2014187886 A2 | 11/2014 |

OTHER PUBLICATIONS

Timo Huttunen: "Ultra-thin X-ray window for detector applications" Dec. 12, 2013 (Dec. 12, 2013)

R. M. Fowler: "Some Recent Developments and Current Problems in Metal Analysis", Analytical Chemistry, vol. 31, No. 12, Dec. 1, 1959 (Dec. 1, 1959), pp. 1949-1951.

O. Bruchwald et al: "Non-destructive in situ monitoring of the microstructural development in high performance steel components during heat treatment", La Metallurgia Italiana, Nov. 1, 2015 (Nov. 1, 2015).

* cited by examiner

DEVICE AND METHOD FOR DETERMINING THE MICROSTRUCTURE OF A METAL PRODUCT, AND METALLURGICAL INSTALLATION

CROSS-REFERENCE TO RELATED APPLICATIONS

The present application is a 371 of International application PCT/EP2017/062527, filed May 24, 2017, which claims priority of DE 10 2016 209 181.6, filed May 25, 2016, and DE 10 2017 208 576.2, filed May 19, 2017, the priority of these applications is hereby claimed and these applications are incorporated herein by reference.

BACKGROUND OF THE INVENTION

The invention relates to a device for determining a microstructure of a metal product during a metallurgical production of the metal product, having at least one x-ray source, at least one x-ray detector, and at least one, preferably closed, receptacle chamber, the x-ray source and/or the x-ray detector being disposed within said receptacle chamber, and said receptacle chamber having at least one window that is permeable to x-ray radiation.

The invention furthermore relates to a metallurgical plant for producing a metal product, having at least one plant electronics unit for controlling and/or regulating an operation of at least one plant component, at least one metallurgical process step being capable of being carried out by way of said plant electronics unit.

The invention further relates to a method for determining a microstructure of a metal product during a metallurgical production of the metal product while using at least one x-ray source and at least one x-ray detector.

Final mechanical properties of a metallurgically produced metal product are part of the substantial quality criteria of such metal products. The microstructure of the metal product is one of the determining factors of said mechanical properties.

Currently, metal products are metallurgically produced by strictly adhering to a proven plan which describes important values for various measured parameters. Conventional measuring technologies acquire parameters such as, for example, a temperature of a metal product, a strip speed, a rolling force, and the like, which to a certain extent are correlated with the microstructure of a metal product. Regular process variations can modify the relationship between the measured parameters and the microstructure of a metal product in such a manner that the metal product can no longer be imparted a desired microstructure and thus not the required mechanical properties. For example, relatively minor deviations of chemical compositions during the production of a dual-phase steel can modify the required temperature profile that is required in order for the desired proportions of austenite and ferrite to be obtained during heat treatment, this leading to metal products which are excessively hard and/or excessively brittle or excessively soft.

The metallurgical production process can be improved when more information pertaining to the microstructure and mechanical properties of a metal product are available during the production of said metal product. This can be achieved, for example by using given measurable parameters such as, for example, a temperature of a metal product, a chemical composition of a metal product, a rolling force, and the like so as to calculate one or a plurality of parameters which heavily correlate with the microstructure and/or mechanical properties of a metal product. However, this disadvantageously requires a process model which necessitates extensive effort in terms of development.

Alternatively, an in-line measuring technology by way of which parameters which heavily correlate with the microstructure of a metal product are measurable can be used. This is likewise demanding since non-destructive, continual, robust and precise measurements are required in a rough environment of production plants.

One potential technology for detecting the microstructure of a metal product is the diffraction of x-rays. The metal product in the case of this technology is radiated by x-rays which, according to Bragg's law, are diffracted on the lattice planes of the crystal structure of the metal product. An x-ray detector detects the intensity of the diffracted x-rays as a function of the diffraction angle. This data can be used so as to obtain parameters which describe the microstructure of the radiated metal product such as, for example, the crystallinity, the phase composition, the granule size, internal and external mechanical stresses and structure of said metal product. Said in-line technology is however not widely used since the measuring apparatuses used herein can be damaged by heat or radiation in the industrial environment of the plant.

Measuring arrangements for measuring properties of a metal strip by means of the diffraction of x-rays are known, for example, from JP 61 010 749 A, JP 03 817 812 B2, and JP 56 001 341 A, DE 38 25 830 C2, EP 0 352 423 B1.

SUMMARY OF THE INVENTION

It is an object of the invention to enable a reliable determination of a microstructure of a metal product during the metallurgical production thereof.

Advantageous design embodiments are set forth in the following description, and the figures, wherein said design embodiments, individually or in various combinations of at least two of said design embodiments, can represent a refining, in particular also preferred or advantageous, aspect of the invention. Design embodiments of the device and of the metallurgical plant herein can correspond to design embodiments of the methods and vice versa, even when reference thereto is not explicitly made in the individual case hereunder.

A device according to the invention for determining a microstructure of a metal product during a metallurgical production of the metal product comprises at least one x-ray source, at least one x-ray detector, at least one, preferably closed, receptacle chamber, the x-ray source and/or the x-ray detector being disposed within said receptacle chamber, and said receptacle chamber having at least one window that is permeable to x-ray radiation, and at least one cooling installation for actively cooling the receptacle chamber.

According to the invention, the receptacle chamber and on account thereof the x-ray source contained therein, or the x-ray detector contained therein, respectively, are actively cooled, this enabling a reliable use of the device according to the invention in a high-temperature environment, under a protective atmosphere, under a heat emission of the metal product, or the like, without the x-ray source, or the x-ray detector, respectively, being damaged by the heat. On account thereof, an in-line determination of the microstructure of a metal product during the metallurgical production thereof, for example in a heat treatment furnace, becomes possible in particular. The receptacle chamber is preferably actively cooled in such a manner that a temperature of the x-ray source, or of the x-ray detector, respectively, at least during the measuring by way of the device, lies below a maximum permissible operating temperature of the x-ray source, or of the x-ray detector, respectively. The receptacle chamber is preferably actively cooled in such a manner that the temperature of the receptacle chamber and thus of the x-ray source disposed therein, or of the x-ray detector disposed therein, respectively, is kept constant such that the measuring conditions are consistent and interferences and deviations which would be caused by temperature variations do not arise.

A quality of the metal product can already be very accurately monitored in the metallurgical production of said metal product by way of this in-line determination of the microstructure of a metal product, on account of which a desired quality level of the metal product can be produced in a reliable and reproducible manner. On account thereof, production rejects can be reduced and production costs can consequently be lowered. Moreover, the production process can be adapted to the respective microstructure of the metal product that has been determined in-line, this increasing the yield and reducing variations in terms of quality and properties of the metal product along the length of the product. Moreover, metal products to be repaired and defective metal products can be removed prior to the further processing thereof and to any transportation to customers, this preventing processing costs and customer claims. Furthermore, an optimization of costs in terms of the processing of metal products can arise, since the direct in-line measurement of the microstructure allows conventionally required safety margins to be relaxed.

The device according to the invention can have an actively cooled receptacle chamber for receiving the x-ray source, and a separate actively cooled receptacle chamber for receiving the x-ray detector. Alternatively, the x-ray source as well as the x-ray detector can be disposed in a single actively cooled receptacle chamber. The device according to the invention can be configured in such a manner that the x-ray source and the x-ray detector are capable of being disposed on the same side or on mutually opposite sides of the metal product. If the x-ray source is disposed in the receptacle chamber, the x-ray radiation that is emitted by the x-ray source passes through the window, hits the metal product, and from the latter makes its way to the x-ray detector (reflection measurement). If the x-ray detector is disposed in a separate receptacle chamber having a window, the x-ray radiation that is diffracted on the metal product makes its way through this window to the x-ray detector. In the case of this radiographic measurement the metal product is completely radiated in the thickness direction. If the x-ray detector is disposed in the same receptacle chamber as the x-ray source, the x-ray radiation that is diffracted on the metal product makes its way through the window of the receptacle chamber to the x-ray detector.

The metal product can be a metal strip, a metal plate, a slab, or a metal product of another elongate configuration. The metal product can in particular be a casting. The metal product can be produced from aluminum, iron, steel, nickel, or copper.

The data acquired by the device according to the invention can be processed in-line and/or off-line. In the case of the latter, the data can be resorted to for optimizing a process model or the like. In the first case, the data by way of data-processing and/or algorithms can be used for controlling and/or regulating parameters of a metallurgical plant used for the production of the metal product. For example, rolling forces, temperatures, temperature ratios, processing or production speeds, and the like, in upstream process steps can be controlled and/or regulated. Said controlling and/or regulating system can be a component part of the device or be implemented in an external system.

According to one advantageous design embodiment the cooling installation comprises at least one supply installation for supplying at least one cooling medium to the receptacle chamber, wherein the receptacle chamber is connected so as to communicate with the supply installation. The cooling medium for cooling herein is guided through the receptacle chamber per se. The supply installation can have an open or a closed cooling medium circuit having at least one pump.

According to one further advantageous design embodiment the cooling installation comprises at least one heat exchanger that is disposed in the receptacle chamber, and at least one supply installation for supplying at least one cooling medium to the heat exchanger, wherein the heat exchanger is connected so as to communicate with the supply installation. On account thereof, the cooling chamber is cooled by means of the heat exchanger. The cooling effect of the cooling installation can be adapted to the respective specific application by way of the choice of the respective cooling medium and by way of a variation of the temperature and/or of the volumetric flow of the cooling medium. The supply installation can have an open or a closed cooling medium circuit having at least one pump. The heat exchanger can be configured, for example, as a cooling serpentine, a cooling coil, a cooling helix, or a planar heat exchanger.

According to one further advantageous design embodiment the cooling installation comprises at least one housing which partially encloses the receptacle chamber and has at least one opening which is closed by the window, and at least one supply installation for supplying at least one cooling medium to the housing, wherein the housing is configured as at least a double wall having mutually spaced apart walls, and at least one intermediate space between walls that are disposed so as to be directly neighboring is connected so as to communicate with the supply installation. The cooling effect of the cooling installation can be adapted to the respective specific application by way of the choice of the cooling medium as well as by way of a variation of the temperature thereof and the volumetric flow thereof. The supply installation can have an open or a closed cooling medium circuit having at least one pump.

According to one further advantageous design embodiment the cooling medium is at least partially liquid and/or gaseous. The choice of the cooling medium depends on the respective specific application.

According to one further advantageous design embodiment the cooling installation comprises at least one regulating installation which has at least one sensor and at least one regulating electronics unit that is connected to the sensor, wherein the regulating electronics unit is specified for actuating the supply installation while taking into account signals of the sensor. On account thereof it is possible for the supply installation and thus the discharge of the thermal energy from the receptacle chamber to be regulated, for example so as to regulate the receptacle chamber to a constant temperature.

According to one further advantageous design embodiment the sensor comprises at least one temperature sensor that is disposed in the receptacle chamber, and/or at least one temperature sensor that measures a temperature of the supplied cooling medium, and/or at least one temperature sensor that measures a temperature of the discharged cooling medium, and/or at least one flow sensor that measures a volumetric flow of the supplied cooling medium, and/or at least one pressure sensor that measures a pressure of the supplied cooling medium, and/or at least one flow sensor that measures a volumetric flow of the discharged cooling medium, and/or at least one pressure sensor that measures a pressure of the discharged cooling medium.

According to one further advantageous design embodiment the regulating electronics unit is specified for actuating the supply installation in such a manner that a temperature of an external face and/or an internal face of the housing lies above a dew point temperature of an atmosphere within and/or outside the housing. On account thereof, the condensation of water close to the sensitive electronics unit within the receptacle chamber, or on the external face of the housing, respectively, is avoided.

According to one further advantageous design embodiment the device comprises at least one installation for drying and/or purifying the supplied cooling medium. It is avoided on account thereof that condensate is created within the receptacle chamber or on the housing, respectively. The cooling medium is preferably in gaseous form and is dried and/or purified by means of the installation so that the dew point temperature of the cooling medium lies below the temperature of the receptacle chamber, or does not entrain any impurities into the receptacle chamber, respectively.

According to one further advantageous design embodiment the window is configured in such a manner that said window at least partially reflects or absorbs incident infrared radiation on the window from outside of the receptacle chamber. It is partially or completely prevented on account thereof that infrared radiation makes its way through the window to the x-ray source, or the x-ray detector, respectively, this preventing any heating of the x-ray source, or the x-ray detector, respectively, by the infrared radiation. The window preferably allows less than 50% of the incident infrared radiation on the window to pass through to the receptacle chamber.

According to one further advantageous design embodiment the window is formed from a polyamide film, or from at least one metal foil, or from glass, or from ceramics, or from a combination of said materials. This prevents that the window enforces a diffraction pattern on the x-ray radiation, which could falsify the measurement by way of the device. A window that is formed from ceramics can withstand the rough environment and can be designed so as to be thin in such a manner that the window absorbs or diffracts x-ray radiation to the least possible extent. The ceramics preferably contains predominantly lightweight elements which interfere with the x-ray radiation to a lesser extent. The window is preferably configured so as to be heat-resistant.

According to one further advantageous design embodiment the window is formed largely from lightweight elements. The material of the window is composed of elements having an atomic number of less than 18 preferably to an extent of more than 50%, particularly preferably of more than 75%, in particular of more than 90%.

According to one further advantageous design embodiment the device comprises at least one motion installation that is connected to the x-ray source and/or the x-ray detector, by way of which motion installation the x-ray source and/or the x-ray detector are/is movable relative to the metal product. On account thereof, the x-ray source and the x-ray detector for measuring can be moved toward the metal product and after measuring be moved away from the metal product, so as to carry out, for example, local measuring and/or for being able to move the x-ray source and/or the x-ray detector to a safe position in hazardous situations. Alternatively or additionally, the x-ray source and the x-ray detector can be moved along a portion of the metal product during measuring. Alternatively or additionally, the x-ray source and the x-ray detector can be moved across part of the width or of the entire width of the metal product during measuring. Alternatively or additionally, the metal product can simultaneously be moved past the device in the longitudinal direction of said metal product, so as to be able to also carry out measuring across a longitudinal portion or the entire length of the metal product. Alternatively or additionally, the receptacle chamber is connected to the motion installation so as to move the x-ray detector and or the x-ray source.

According to one further advantageous design embodiment the device comprises at least one rinsing installation which is connected so as to communicate with the receptacle chamber and by way of which the receptacle chamber is capable of being rinsed with at least one rinsing medium. A deposition of dust or other contaminations on the x-ray source, or the x-ray detector, respectively, which could compromise the functioning of the device can be removed and/or prevented on account thereof.

According to one further advantageous design embodiment the rinsing medium is at least partially liquid and/or gaseous. The choice of the cooling medium depends on the respective specific application. A dried and/or purified and/or cooled rinsing medium is preferably used.

A metallurgical plant according to the invention for producing a metal product comprises at least one plant electronics unit for controlling and/or regulating an operation of at least one plant component, at least one metallurgical process step being capable of being carried out by way of said plant electronics unit, and at least one device according to one of the aforementioned design embodiments or any arbitrary combination of at least two of said design embodiments that is connected to the plant electronics unit, wherein the plant electronics unit is specified for determining the microstructure of the metal product from signals of the device, and for controlling and/or regulating the plant component while taking into account the determined microstructure.

The advantages that have been mentioned above in the context of the device are associated in an analogous manner with the metallurgical plant. The metallurgical plant according to the invention is operated while taking into account data that is detected in-line by means of the device. The plant component can be, for example, a rolling mill, a heat treatment furnace, a cooling line, or the like.

According to a method according to the invention for determining a microstructure of a metal product during a metallurgical production of the metal product while using at least one x-ray source and at least one x-ray detector, the x-ray source and/or the x-ray detector are/is actively cooled during the determination of the microstructure of the metal product.

The advantages that have been mentioned above in the context of the device are associated in an analogous manner with the method. The device according to one of the above-mentioned design embodiments or any arbitrary combination of at least two of said design embodiments can in particular be used for carrying out the method.

BRIEF DESCRIPTION OF THE DRAWING

The invention will be explained in an exemplary manner hereunder with reference to the appended figures and by means of preferred embodiments, wherein the features explained hereunder can individually as well as in various combinations represent an advantageous or refining aspect of the invention. In the figures.

DETAILED DESCRIPTION OF THE INVENTION

Figure 1:
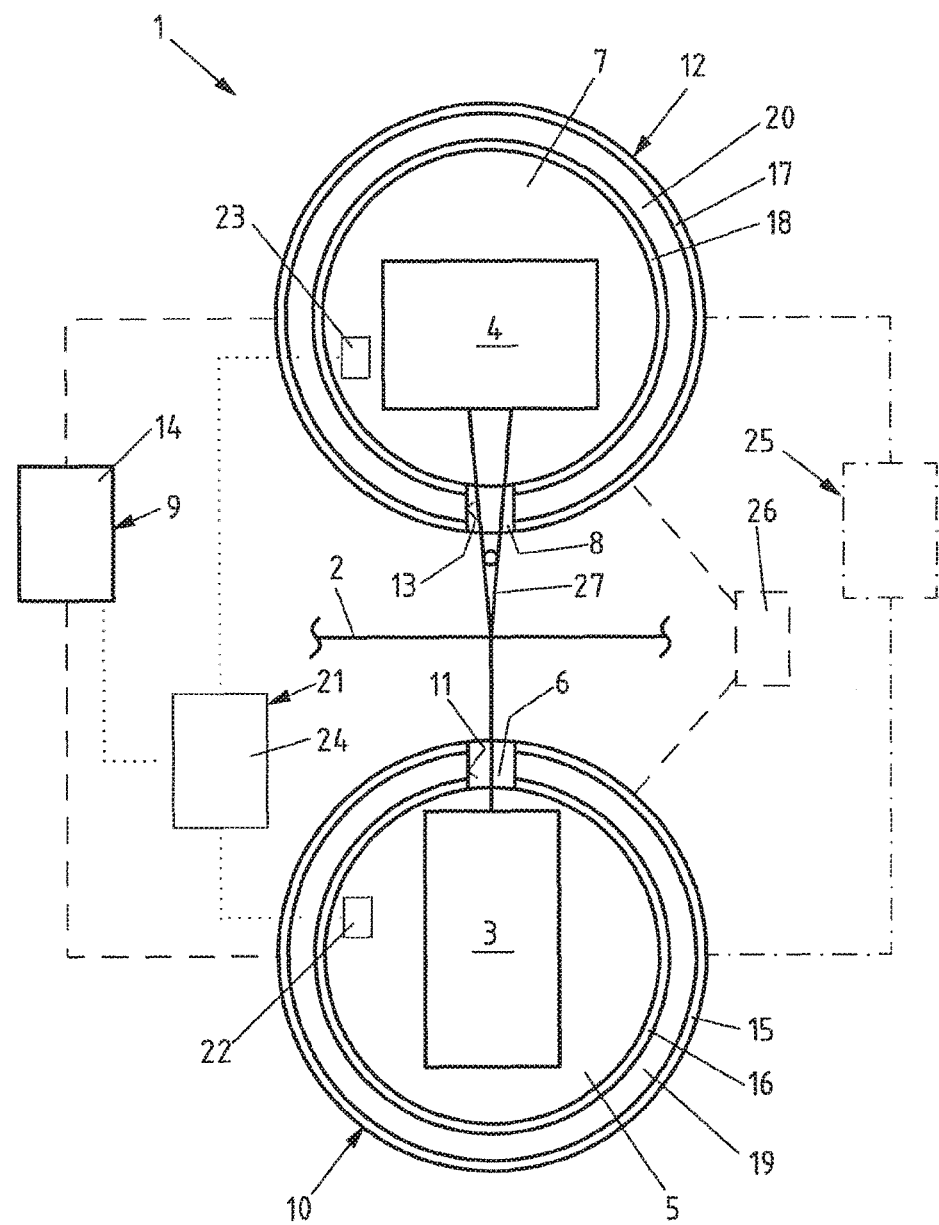
FIG. 1 shows a schematic illustration of an exemplary embodiment for a device according to the invention.

FIG. 1 shows a schematic illustration of an exemplary embodiment for a device 1 according to the invention for determining a microstructure of a metal product 2 during a metallurgical production of the metal product 2.

The device 1 comprises an x-ray source 3 that is disposed on one side of the metal product 2, and an x-ray detector 4 that is disposed on the opposite side of the metal product 2. The device 1 furthermore comprises a, preferably closed, receptacle chamber 5 within which the x-ray source 3 is disposed and which has a heat-resistant window 6 that is permeable to x-ray radiation. The device 1 moreover comprises a further, preferably closed, receptacle chamber 7 within which the x-ray detector 4 is disposed and which has a heat-resistant window 8 that is permeable to x-ray radiation. Each window 6 or 8, respectively, can be configured in such a manner that said window partially or completely reflects incident infrared radiation on said window 6 or 8, respectively, from outside of the respective receptacle chamber 5 or 7, respectively. Moreover, each window 6 or 8, respectively, can be formed from a polyamide film, or from at least one metal foil, or from glass, or from ceramics, or the like, or from a combination of said materials. The materials are preferably amorphous.

The device 1 comprises a cooling installation 9 for actively cooling the receptacle chambers 5 and 7. The cooling installation 9 comprises a housing 10 which partially encloses the receptacle chamber 5 and which has at least one opening 11 which is closed by the window 6. The cooling installation 9 moreover comprises a housing 12 which partially encloses the receptacle chamber 7 and which has at least one opening 13 which is closed by the window 8. The cooling installation 9 furthermore comprises a supply installation 14 for supplying a cooling medium to the housings 10 and 12. Each housing 10 or 12, respectively, is configured as a double wall having walls 15 and 16, or 17 and 18, respectively, that are disposed so as to be mutually spaced apart. An intermediate space 19 or 20, respectively, between walls 15 and 16, or 17 and 18, respectively, that are disposed so as to be directly neighboring is connected so as to communicate with the supply installation 14. The cooling medium is at least partially liquid or gaseous.

The cooling installation 9 can have a regulating installation 21 which is schematically indicated by dashed lines and which has a sensor 22 that is disposed in the receptacle chamber 5, a sensor 23 that is disposed in the receptacle chamber 7, and a regulating electronics unit 24 that is connected to the sensors 22 and 23, wherein the regulating electronics unit 24 is specified for actuating the supply installation 14 while taking into account signals of the sensors 22 and 23. The sensors comprise at least one temperature sensor that is disposed in the receptacle chamber, or a temperature sensor for the incoming cooling medium, or a temperature sensor for the outgoing cooling medium, or a flow sensor for the incoming cooling medium, or a flow sensor for the outgoing cooling medium, or a combination of said sensors. The regulating electronics unit 24 can be specified for actuating the supply installation 14 in such a manner that a temperature of an external face and/or an internal face of the respective housing 10 or 12, respectively, lies above a dew point temperature of an atmosphere within and/or outside the housings 10 and 12.

The device 1 can have a motion installation 25 which is indicated in a schematic manner by dashed lines, which by way of the respective housing 10 or 12, respectively, is connected indirectly to the x-ray source 3 and the x-ray detector 4, and by which the x-ray source 3 and the x-ray detector 4 are movable relative to the metal product 2.

The device 1 can furthermore have a rinsing installation 26 which is schematically indicated by dashed lines and which is connected so as to communicate with the receptacle chambers 5 and 7, and by which the receptacle chambers 5 and 7 are capable of being rinsed with a rinsing medium in that the rinsing medium is blown through the receptacle chambers 5 and 7. The rinsing installation 26 is preferably directed toward the respective window 6, respectively, so as to blow away impurities such as dust and the like.

The x-ray source 3 for determining the microstructure of the metal product 2 emits x-ray radiation 27 which impacts the metal product 2 through the window 6 and is diffracted by said metal product 2. The diffracted x-ray radiation enters the receptacle chamber 7 through the window 8 and is detected by the x-ray detector 4 in said receptacle chamber 7.

Alternatively or additionally, the cooling installation 9 can have two heat exchangers 32 and 33 which are in each case disposed in a receptacle chamber 5 or 7, respectively. The supply installation 14 in such a case can be specified for supplying at least one cooling medium to the heat exchangers 32 and 33, to which end the heat exchangers 32 and 33 can be connected so as to communicate with the supply installation 14.

Figure 2:
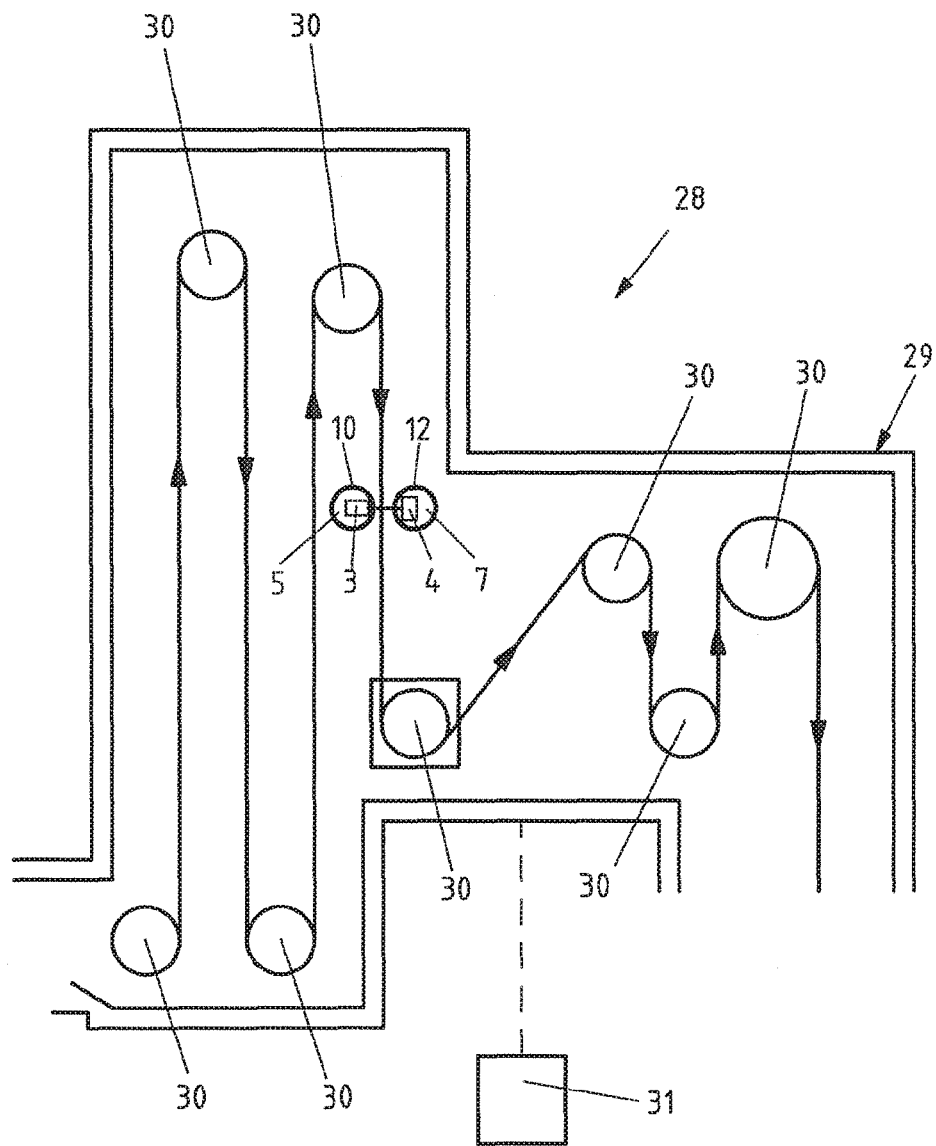
FIG. 2 shows a schematic illustration of an exemplary embodiment for a metallurgical plant according to the invention.

FIG. 2 shows a schematic illustration of an exemplary embodiment for a metallurgical plant 28 according to the invention for producing a metal product 2 in the form of a metal strip. A heat treatment furnace 29 of the metallurgical plant 28 is shown, the metal product 2 that is guided by way of deflection rollers 30 being guided through said heat treatment furnace 29. High temperatures prevail within the heat treatment furnace 29.

The metallurgical plant 28 comprises a plant electronics unit 31 for controlling and/or regulating an operation of at least one plant component, in particular the heat treatment furnace 29, a metallurgical process step being capable of being carried out by way of said plant component or said heat treatment furnace 29, respectively.

The metallurgical plant 28 furthermore comprises a device 1 for determining a microstructure of the metal product 2 during a metallurgical production of the metal product 2, said device 1 being connected to the plant electronics unit 31, wherein the device 1 is configured according to FIG. 1. In order for repetitions to be avoided, reference in terms of device 1 is made to the above description pertaining to FIG. 1. The plant electronics unit 31 is specified for determining the microstructure of the metal product 2 from signals of the device 1, and for controlling and/or regulating the plant component, thus the heat treatment furnace 29, while taking into account the determined microstructure.

LIST OF REFERENCE SIGNS

1 Device
2 Metal product

3 X-ray source
4 X-ray detector
5 Receptacle chamber
6 Window
7 Receptacle chamber
8 Window
9 Cooling installation
10 Housing
11 Opening of 10
12 Housing
13 Opening of 12
14 Supply installation
15 Wall of 10
16 Wall of 10
17 Wall of 12
18 Wall of 12
19 Intermediate space of 10
20 Intermediate space of 12
21 Regulating installation
22 Temperature sensor
23 Temperature sensor
24 Regulating electronics unit
25 Motion installation
26 Rinsing installation
27 X-ray radiation
28 Metallurgical plant
29 Heat treatment furnace
30 Deflection roller
31 Plant electronics unit
32 Heat exchanger
33 Heat exchanger

The invention claimed is:

1. A device for determining a microstructure of a metal product during a metallurgical production of the metal product, said device comprising: at least one x-ray source; at least one x-ray detector; at least one receptacle chamber, the x-ray source and/or the x-ray detector being disposed within said receptacle chamber, and said receptacle chamber having at least one window that is permeable to x-ray radiation; at least one cooling installation for actively cooling the receptacle chamber, wherein the cooling installation includes at least one supply installation for supplying at least one cooling medium to the receptacle chamber, wherein the receptacle chamber is connected so as to communicate with the supply installation, wherein the cooling installation further includes at least one regulating installation which has at least one sensor and at least one regulating electronics unit that is connected to the at least one sensor, wherein the regulating electronics unit is configured to actuate the at least one supply installation in response to signals of the at least one sensor, wherein the cooling installation has a housing and the regulating electronics unit is configured to actuate the at least one supply installation so that a temperature of an external face and/or an internal face of the housing lies above a dew point temperature of an atmosphere within and/or outside the housing, wherein the window is configured to reflect or absorb incident infrared radiation on the window from outside of the receptacle chamber so that less than 50% of the incident infrared radiation on the window passes through to the receptacle chamber, wherein the housing is configured as at least a double wall structure having mutually spaced apart walls.

2. The device according to claim 1, wherein the cooling installation includes at least one heat exchanger disposed in the receptacle chamber, wherein the at least one supply installation supplies at least one cooling medium to the heat exchanger, wherein the heat exchanger is connected so as to communicate with the supply installation.

3. The device according to claim 1, wherein the housing partially encloses the receptacle chamber and has at least one opening which is closed by the window, wherein the at least one supply installation supplies at least one cooling medium to the housing, wherein at least one intermediate space between walls that are disposed so as to be directly neighboring is connected so as to communicate with the supply installation.

4. The device according to claim 1, wherein the cooling medium is at least partially liquid and/or gaseous.

5. The device according to claim 1, wherein the at least one sensor is a temperature sensor disposed in the receptacle chamber, and/or a temperature sensor that measures a temperature of the supplied cooling medium, and/or a temperature sensor that measures a temperature of the discharged cooling medium, and/or a flow sensor that measures a volumetric flow of the supplied cooling medium, and/or a pressure sensor that measures a pressure of the supplied cooling medium, and/or a flow sensor that measures a volumetric flow of the discharged cooling medium, and/or a pressure sensor that measures a pressure of the discharged cooling medium.

6. The device according to claim 1, further comprising at least one installation for drying and/or purifying the supplied cooling medium.

7. The device according to claim 1, wherein the window is formed from a polyamide film, at least one metal foil, glass, or ceramics, or a combination of said materials.

8. The device according to claim 1, wherein the window is formed largely from lightweight elements.

9. The device according to claim 1, further comprising at least one motion installation connected to the x-ray source and/or the x-ray detector, by way of which motion installation the x-ray source and/or the x-ray detector are/is movable relative to the metal product.

10. The device according to claim 1, further comprising at least one rinsing installation connected so as to communicate with the receptacle chamber and by way of which the receptacle chamber is rinsed with at least one rinsing medium.

11. The device according to claim 10, wherein the rinsing medium is at least partially liquid and/or gaseous.

12. A metallurgical plant for producing a metal product, comprising: at least one plant electronics unit for controlling and/or regulating an operation of at least one plant component, the electronics unit being configured to carry out at least one metallurgical process step; and at least one device according to claim 1 connected to the plant electronics unit, wherein the plant electronics unit is configured to determine a microstructure of the metal product from signals of the device, and to control and/or regulate the plant component while taking into account the determined microstructure.

* * * * *